United States Patent [19]

Solenberg

[11] Patent Number: 5,382,527
[45] Date of Patent: Jan. 17, 1995

[54] TRANSPOSABLE ELEMENTS FROM STREPTOMYCES AND OTHER ORGANISMS

[75] Inventor: Patricia J. Solenberg, Indianapolis, Ind.

[73] Assignee: Eli Lilly and Company, Indianapolis, Ind.

[21] Appl. No.: 138,329

[22] Filed: Oct. 18, 1993

Related U.S. Application Data

[60] Division of Ser. No. 898,353, Jun. 12, 1992, Pat. No. 5,264,354, which is a continuation of Ser. No. 252,095, Sep. 30, 1988, abandoned.

[51] Int. Cl.$^6$ .................... C12N 15/11; C12N 15/76
[52] U.S. Cl. .................................. 435/320.1; 536/23.1
[58] Field of Search ...................... 536/23.1; 435/320.1

[56] References Cited

U.S. PATENT DOCUMENTS

| | | | |
|---|---|---|---|
| 4,650,361 | 3/1987 | Hershberger et al. | 435/172.3 |
| 4,843,002 | 6/1989 | Rao et al. | 435/172.3 |

OTHER PUBLICATIONS

Raabe et al., 1988, *Mol. Gen. Genet.* 215:176–180.
Scordilis et al., 1987, *J. Bact.* 169(1):1–8.
Bishop et al., 1984, *Mol. Gen. Genet.* 196:117–122.
Larson et al., 1986, *Plasmid* 15: 199–209.
Maniatis et al., 1982, *Molecular Cloning*, Cold Spring Harbor Laboratory, N.Y. pp. 17–54.
Sugimoto et al., 1985, *Appl. Microbiol. Biotechnol.* 22:336–342.
Birch et al., 1985, *J. Gen. Micro.* 131:1299–1303.
Tanaka et al., 1988, 7th International Symposium on the Biology of Actinomycetes, Tokyo, Japan Abstract pp. 5–20.
Tanaka et al., 1987, *J. Pharm. Sci.* 76(11):S185.
Olson et al., 1988, *J. Bacteriol.* 170:1955–1957.
Chung, S. T., 1987, *J. Bacteriol.* 169:4436–4441.
Chater et al., 1985, *Mol. Gen Genet.* 200:235–239.
Bruton et al., 1987, *Nuc. Acids Res.* 15:7053–7065.
Sermonti et al., 1983, *Mol. Gen. Genet.* 191:158–161.

*Primary Examiner*—Richard A. Schwartz
*Assistant Examiner*—Gary L. Brown
*Attorney, Agent, or Firm*—Douglas K. Norman; Gerald V. Dahling

[57] ABSTRACT

A novel method for isolating transposable elements was used to isolate an approximately 1.6 kb insertion sequence from Streptomyces. The method entails transforming a cell with a plasmid containing a repressor gene, so that the introduction of a transposable element into the gene allows the expression of a selectable marker in a second host cell. The novel insertion sequence isolated from *Streptomyces lividans* CT2 has been designated IS493.

11 Claims, 8 Drawing Sheets

TRANSPOSABLE ELEMENTS FROM STREPTOMYCES AND OTHER ORGANISMS

This application is a division of application Ser. No. 07,898,353, filed Jun. 12, 1992, now U.S. Pat. No. 5,264,354 which is a continuation of application Ser. No. 07/252,095, filed Sep. 30, 1988 now abandoned.

The present invention comprises a novel method for isolating transposable elements from a wide variety of cell sources. Transposable elements, such as transposons, insertion sequences, or transposing bacteriophages, are found in both prokaryotic and eukaryotic cells. These elements are capable of insertion events at few or many different sites along the genome. This ability to transpose and insert, even in the absence of DNA homology, has allowed transposable elements to be exploited as powerful genetic tools. Some examples of the utility of such elements include gene mapping, use as promoter probes, construction of insertion mutations, the mediation of intergeneric recombination, the insertion of genetic information into the genome of a recipient strain and the genetic tagging of specific genes.

In the past, transposable elements from Streptomyces were isolated only after serendipitous events such as a noted increase in plasmid or phage size. Such occurrences are relatively rare, as most prokaryotic transposable elements transpose at rates of $10^{-4}$ to $10^{-7}$ per generation. The present invention enables the scientist to select for and identify these rare events and provides an easy, systematic method for the large-scale isolation of useful transposable elements, particularly in the large and industrially important group of organisms known as Streptomyces.

The development and exploitation of recombinant DNA technology in Streptomyces depends upon the availability of genetic tools for the introduction of foreign DNA or of multiple copies of native DNA into the genome of these cells. This development has been retarded by the very low number of transposable elements presently available for use in Streptomyces. The present invention is useful and especially important in that it allows the rapid and systematic search for such useful genetic tools. It is important to have the ability to isolate a variety of transposable elements since different elements tend to have different characteristics. It is these different characteristics such as transposition frequency, target site specificity, and transposition mechanisms that make particular elements useful for particular genetic manipulations. As the number of transposable elements from Streptomyces increases due to the method of the present invention, so too will the ability to conveniently alter Streptomyces cells increase. Therefore, the present invention allows for the introduction of a variety of new and useful genetic tools and cloning systems in this commercially important group. These new genetic tools will allow for the genetic manipulation of these organisms and analysis of metabolic pathways and genetic organization. Furthermore, the discovery of new transposable elements will facilitate the cloning of genes both for increasing the yields of known antibiotics and other useful metabolites and also for producing new antibiotics and other new metabolic derivatives.

The present invention also provides a transposable element from Streptomyces which was specifically isolated by employing the novel method disclosed herein. This element is useful for insertionally inactivating chromosomal genes as well as for inserting any sort of foreign DNA into the Streptomyces genome. The invention therefore helps to fulfill the long-felt need for such discrete, clearly defined elements for use in Streptomyces, thereby releasing the skilled artisan from reliance upon extra-chromosomal elements or homologous integration.

For purposes of the present invention, as disclosed and claimed herein, the following terms are defined below.

$Am^R$—the apramycin-resistant phenotype or gene conferring same.

$Ap^R$—the ampicillin-resistant phenotype or gene conferring same.

Gene—a DNA segment which encodes a promoter function, a ribosome binding site and a translatable gene product.

Insertion sequence—small (generally less than 2000 bp) elements which encode no known genes unrelated to insertion function.

Ori—an origin of replication.

Origin of replication—a DNA sequece which allows the replication of an extrachromosomal element in a specific host cell.

Recombinant DNA cloning vector—any autonomously replicating agent, including, but not limited to plasmids and phages, comprising a DNA molecule to which one or more additional DNA segments can be or have been added.

Repressor—a protein which represses or prevents expression of specific gene products.

Selectable marker—a gene or combination of genes of known function, the expression of which can be easily determined.

Transduction—the introduction of DNA into a recipient host cell via a phage.

Transfection—the introduction of DNA into a recipient host cell via phage DNA.

Transformation—the introduction of DNA into a recipient host cell via a plasmid.

Transposable element—a transposon, an insertion sequence, a transposing bacteriophage or a discrete piece of double standed DNA which is capable of insertion at few or many sites in a genome.

Transposon—a transposable element, generally larger than 2 kb that may contain additional determinants unrelated to insertion function such as antibiotic or heavy metal resistance-conferring genes or biosynthetic genes.

$Tsr^R$—the thiostrepton resistant phenotype or gene conferring same.

DETAILED DESCRIPTION OF THE INVENTION

Figure 1:
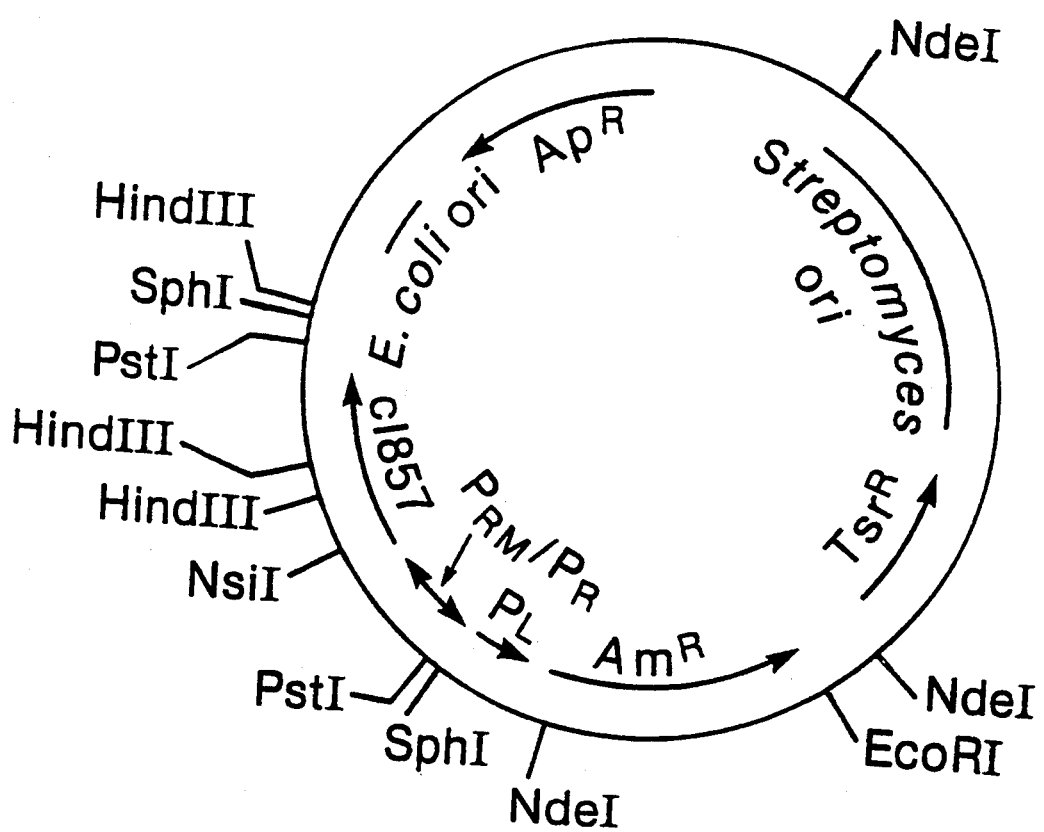
FIG. 1—the restriction site and function map of plasmid pCZA126. For the purposes of this disclosure, the Figures are not drawn exactly to scale.

The present invention is a method for screening a cell culture for a transposable element, said method comprising:
  (a) transforming, transfecting or transducing a culture of a first host cell with a recombinant DNA cloning vector, said vector comprising
    (1) a DNA segment which comprises an gene that encodes a repressor function,
    (2) a repressible promoter which is is not functional in a second host cell when said repressor function is expressed and which is functional in a second host cell when said repressor function is not expressed,
    (3) a selectable marker, the expression of which is driven by said promoter,
    (4) an origin of replication which is functional in a second host cell,
    (5) a second origin of replication which is functional in the first host cell, and
  (b) culturing said host cell transformed, transfected or transduced in step (a) under conditions suitable for the introduction of a transposable element into said DNA segment comprising a gene that encodes a repressor function in said second host cell,
  (c) transforming, transfecting or transducing a culture of said second host cell with recombinant DNA cloning vector DNA isolated from the host cells cultured in step (b), and
  (d) determining whether said culture of a first host cell comprises a transposable element by culturing said culture of a second host cell transformed, transfected or transduced in step (c) under conditions selective for the expression of said marker contained in the vector of step (a),
subject to the limitation that said first and second host cells are susceptible to transformation, transfection or transduction.

The present invention further comprises a method for selecting host cells which contain vectors comprising transposable elements as well as a method for isolating such transposable elements from such vectors. Such methods of isolating transposable elements may be accomplished by transducing, transfecting or transforming a first host cell with a recombinant DNA cloning vector containing a repressor gene that functions in a second host cell, a promoter which is sensitive to the repressor protein in the second host cell, a selectable marker driven by said promoter and an origin of replication that is functional in the second host cell. Upon reisolation and back-transformation of the cloning vector into the second host cell, those clones which contain a repressor gene interrupted by a transposable element can be selected because transcription of the selectable marker is no longer repressed. The invention can also be practiced by employing a vector which further comprises a second selectable marker which is functional in the second host cell in the presence of the expressed repressor function. Such a vector is particularly useful in comparing transformation efficiency to efficiency of "trapping" transposable elements. Furthermore, the vector can also comprise a third selectable marker which is functional in the first host cell, thereby allowing selection of transfectants, transformants or transductants after the first introduction of the vector into the first host cell. It is also possible to use selectable markers which are functional in both the first and second host cells for purposes of the present invention.

The present invention is best exemplified by the use of plasmid pCZA126. Plasmid pCZA126 contains the $P_R$ and $P_L$ repressible promoters from bacteriophage lambda operating in tandem to drive the expression of an apramycin resistance-conferring gene. Plasmid pCZA126 also contains the bacteriophage lambda cI857 repressor gene which, when functioning, produces a repressor function in $E.$ $coli$ so that the tandem $P_RP_L$ promoters cannot promote the expression of the apramycin resistance-conferring gene. If the promoter, ribosome binding site, or translatable sequence of the cI857 repressor gene is disrupted, the repressor function will be inactivated and the lambda PRPL promoters will then promote the expression of the apramycin resistance-conferring gene. The coding region of the apramycin resistance-conferring gene is from pKC462A. (NRRL B-15983).

In addition to the above-mentioned elements, plasmid pCZA126 also contains the ColE1 origin of replication and ampicillin resistance-conferring gene of plasmid pBR322, and the SCP2* derivative origin of replication and thiostrepton resistance-conferring gene of plasmid pHJL400 (Larson and Hershberger, 1986, Plasmid 15: 199–209). A restriction site and function map of plasmid pCZA126 is presented in FIG. 1 of the accompanying drawings. Plasmid pCZA126 can be obtained from $E.$ $coli$ K12 JM109/pCZA126, a strain deposited and made part of the permanent stock culture collection of the Northern Regional Research Laboratory (NRRL), Agricultural Research Service, 1815 North University Street, U.S. Department of Agriculture, Peoria, Ill. 61604. It is available to the public as a source and stock reservoir of the plasmid under the accession number NRRL B-18416.

Plasmid pCZA126 was first transformed into $Streptomyces$ $lividans$ CT2, a strain also deposited with the above mentioned NRRL under the accession number NRRL 18418. The transformants were selected on media containing thiostrepton, then the plasmid DNA was isolated from the transformants and back-transformed into $E.$ $coli$ K12 JM109 cells. Any disruption of the cI857 gene results in the conversion of the transformed $E.$ $coli$ cells to apramycin resistance. An apramycin resistant colony was selected and restriction enzyme analysis of the constituent plasmid revealed an approximately 1.6 kb insertion within the cI857 gene. Further sequence analysis and Southern hybridization analysis showed the insert to be an insertion sequence of $S.$ $lividans$ CT2 origin.

It will be understood that the various elements of the vector used in the present invention are in no way limited to those exemplified herein. For example, eukaryotic transposable elements may be isolated by shuttling the vector into various eukaryotic cells. When probing for yeast elements, for example, one can use the origin of replication from yeast plasmid YEP24 and the URA3 or LEU2 selectable markers. The cells of multicellular organisms may also be screened for the presence of transposable elements by substitution of the various elements of the desired vector. Rubin et al., U.S. Pat. No. 4,670,388 disclose various phages and selectable markers which are useful in Drosophila genetics. These factors can easily be transferred into a vector of the present invention to allow for screening of Drosophila for transposable elements.

In addition to the substitution of various elements to allow screening in other genera, the elements may also be substituted to increase the ease or efficiency of screening in Streptomyces species. For example, the Streptomyces origin of replication from pHJL400 which is present in pCZA126 can be easily replaced by one of many origins of replication known to those skilled in the art. Table 1 is an illustrative, but not comprehensive, listing of Streptomyces plasmids from which additional, functional Streptomyces origins of replication can be obtained. Those skilled in the art recognize that all or part of the plasmids may be used to construct vectors exemplifying the present invention so long as the origin of replication function is not disrupted. The plasmid containing host and depository accession number are also listed in Table 1.

TABLE I

Streptomyces Plasmids

| Plasmid | Host | Accession Number |
|---------|------|------------------|
| SCP2 | Streptomyces coelicolor A3(2) | NRRL 15042 |
| pEL7 | Streptomyces ambofaciens | NRRL 12523 |
| SLP1 | Streptomyces lividans | NCIB[1] 11417 |
| pNM100 | Streptomyces virginiae | NRRL 15156 |
| pEL103 | Streptomyces granuloruber A39912.13/pEL103 | NRRL 12549 |
| pIJ702 | Streptomyces lividans | ATCC[2] 39155 |

[1]National Collection of Industrial Bacteria (NCIB), Torry Research Station, Post Office Box 31, 135 Abbey Road, Aberdeen AB98DG, Scotland, United Kingdom
[2]American Type Culture Collection (ATCC), 12301 Parklawn Drive, Rockville, Maryland 20582, United States of America Other origins of replication such as SLP1.2 (Horinouchi et al., 1985, *J. Bacteriol.* 162: 406), pSRC1-b (Shindoh et al., 1984, *J. Antibiot.* 37: 512), pSL1 (Nakano et al., 1982, *FEMS Microbiol. Lett.* 13: 279) and pSF765 (Murakami et al., 1983, *J. Antibiot.* 36: 429) may also be used for constructing vectors within the scope of the present invention.

Skilled artisans will also recognize that many different origins of replication are available for use in *E. coli*. Since the presence of a particular *E. coli* origin of replication is not a critical component of the present invention, the substitution of functional origin of replication-containing and, if desired, antibiotic resistance-conferring restriction fragments from *E. coli* plasmids such as, for example, pCZ101 (Schoner et al., 1984, *Proc. Natl. Acad. Sci. USA* 81: 5403), pACYC184, pBR325, pBR328 and the like can also be used for purposes of the present invention. Various selectable markers may also be substituted for the antibiotic resistance-conferring genes exemplified herein. For example, colorimetric markers such as the β-galactosidase system or nutritional markers such as the yeast URA3 or LEU2 genes may be employed. Many different antibiotic resistance conferring genes may also be employed in the vector of the present invention, such as, but not limited to, the tylosin, spiramycin, carbomycin or picromycin resistance-conferring genes of various Streptomyces species. There are also many different antibiotic-resistance conferring genes which are functional in *E. coli*, such as the kanamycin and tetracycline resistance-conferring genes, to name but a few. Some genes, such as the native *E. coli* apramycin resistance-conferring gene, are functional in both *E. coli* and Streptomyces. Skilled artisans will understand that all of these genes can be used, alone or in combination, for purposes of further exemplifying the present invention.

The repressor/promoter system of the illustrative vector used in the present method may also be altered according to the needs of the skilled artisan. For example, those systems which require incubation at 37° C. should utilize the bacteriophage λ cI repressor, as opposed to the cI857 repressor which does not function well at temperatures near 37° C. The lacZ repressor/promoter system could also be used in the present invention. Furthermore, the sequence encoding the repressor function could easily be changed, so long as the alternate sequence still encodes a functional repressor. Such an alternative sequence would provide alternate target sites for transposition events. Skilled artisans recognize that many different combinations of all the aforementioned elements of the vector are possible and therefore the present method is useful in a wide variety of primary and secondary host cells. A very versatile transposon trap plasmid may have several origins of replication that function in various species. Accordingly, the invention can easily be practiced in both eukaryotic and prokaryotic systems and therefore is in no way limited by the examples set forth below.

The present invention further comprises a newly isolated insertion element, designated IS493. The nucleotide sequence of IS493 comprises:

| | | | | | |
|---|---|---|---|---|---|
| 5'- | AGCGTTTTCC | ATCCTCAAGC | TGAGCTGGCC | TGATGCAGGC | AGAGGACGGC |
| 51 | CTGGACGAGG | ACCGTGACGC | GGGTGGTCGA | GCAACGGAGC | CTGCGAAGGA |
| 101 | GTCGCCAGGA | CTTGAGGGTC | GCGACGGCTT | GCTCGACGAG | CGCCCGGATC |
| 151 | TTCGCGTGGG | ATCGATTGAC | GGCCTGCTGC | CCTGCAGAGA | GCGTCTCCCA |
| 201 | CCGGCCGCGG | TAGGGAACAC | GGACCGTGCC | TCCGGCGCCC | TGGTAGCCCT |
| 251 | TGTCTGCCCA | GCAGTTGACG | TCGGCTGTGG | CAAGCGTGTC | GATGATGCCG |
| 301 | TGCTCGCGGG | CCGCACGGAC | GTCGTGGACG | GCTCCGGGCA | GGGCCGGCGA |
| 351 | GGCCCACAGC | AGGCGGCCGG | AAGGATCTGC | GATCACCTGT | ACGTTCATCC |
| 401 | CGTGTTTCTT | GTGCTTGCCC | GAGTAGAAAG | GCCGGTCGGC | GGCGATTCGG |
| 451 | TCGATCGGCA | GCAGCGTCCC | GTCCAGCAGG | ACGAACGCCT | TCATCGACGC |
| 501 | CGCCCGGACC | GCCTCGGCGA | GCGTCGGGGC | AAGGGCGGCC | AGAACCTCAG |
| 551 | CTGCCTCGGT | GACGTAGCGG | TAGGCAGTGG | TGGTGCCCAC | GCCGAACCCG |
| 601 | GCCGCGAGCT | GCACATACGG | ATGACCGTTG | CGGAGATGGG | CGAGGGCGAG |
| 651 | CAGAGCCTGC | CGACCTGCGC | TCAGGCGCCG | CCACCGGGTG | CCGAGACCAC |
| 701 | GGCGGTGTTC | CCGCAGACGG | GCGGAGAGGA | AGCGGAGGGC | AGAACTGGAC |
| 751 | ACGTCCAGCC | CGGAGGGGTA | AACAAGCACG | TGAAGCCTCT | AGTAGAGACG |
| 801 | GATTTCTTGG | TCGAAAACCC | ATCTACCAGG | GGCTTCACCC | CTGTGTCAGG |
| 851 | CCAACCCGCA | AGCTGCCGAA | GCAGAATGAA | GACGCTCCTT | GGCTACCGGT |
| 901 | CTGGCGCATG | CGAACCCCGA | CGTCGTGGGT | CTAGCTGGTT | GTCCTGACGG |
| 951 | GTGCGCTGCT | GCGCCCGTGG | CGTCGACCGC | TGAGCTGGC | GTCGAGTGTC |
| 1001 | TCCTGAGCCA | CGCGCATGGC | CTCGGCGTAT | ACGGGGTCCT | GCAGCCGCTT |
| 1051 | CCACATCTCG | CCCTCAGAGA | CGTCCTCAAC | GCAGCTGACC | ACCCACCAGA |
| 1101 | TATTGCCGAA | GGGGTCCTTG | ATGCGCCCTC | CGCGCTGTCC | GAAGGCGTCG |

| | | | | |
|---|---|---|---|---|
| 1151 | TCGGCCAGGG | AAGTGACGAC | ATAGCCGCCA | GCTGCGACGG | CCTGGGAAAA |
| 1201 | CGCCTCGTCC | GCATCGGCGA | CAAATACGCG | CAGCAGGCTC | GGCATGGCGG |
| 1251 | GCCAGTCCGT | GTGTCGGTCG | AAGGCCAACA | CGACGGTGTC | GCCGACTCGG |
| 1301 | ATCTCAGCGT | GACCGATCAA | GCCCTCCTCG | GTCGACACCC | GCCCGAGTTC |
| 1351 | CTCGCCCCCG | AATGCCTGGG | TGACGAAGTC | GAGGAAAGCC | CCCGTGTCGT |
| 1401 | CGGTGACGAC | CCAGGGCGCA | ACGGTGGTGT | AGCCCTCCGG | CTCGGGGCTG |
| 1451 | GTCTGCTGGG | GCATCGCGGT | CCTTTCGCTG | ATGTTGCTTG | CCAGCAGCGA |
| 1501 | CGGTAGGCGT | GAGCTAGGGT | CAGCTTCTGT | CCTAGACGGC | AGTGAGCTTC |
| 1551 | GAGCGCAACC | GGTACTACCT | CACGACCGCT | CGCGCTGATC | CAGACCCCGC |
| 1601 | CTCTGACCCC | TGACCCCGTC | AGCCTGAGGT | TGAAAACGC | T-3' | wherein A is deoxyadenyl, G is deoxyguanyl, C is deoxycytidyl, and T is thymidyl.

Figure 2:
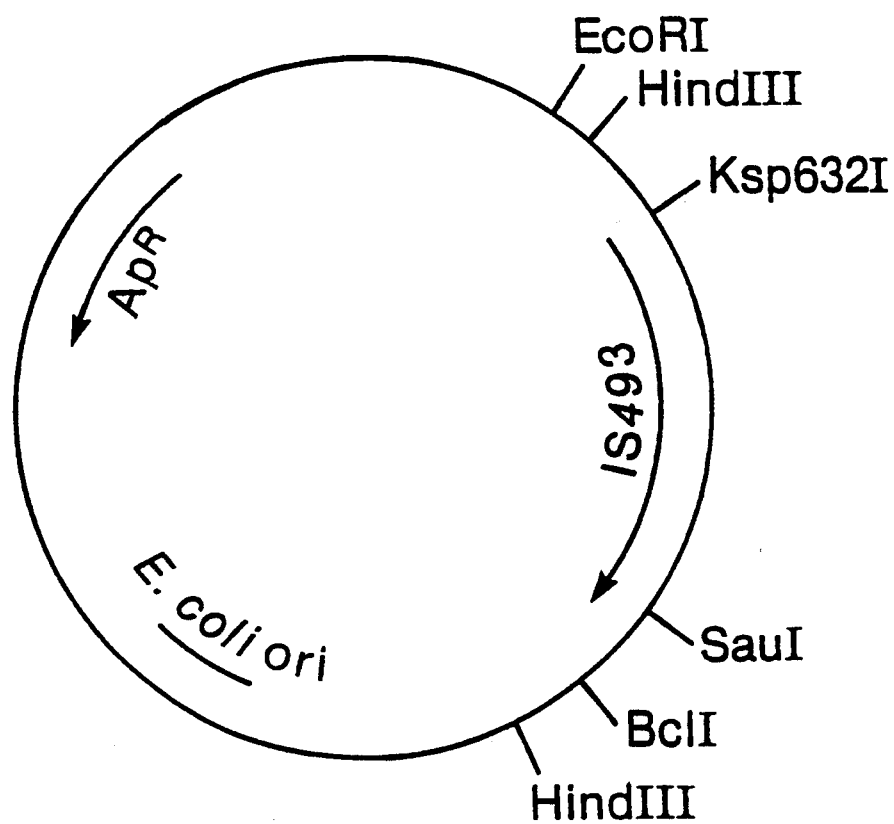
FIG. 2—the restriction site and function map of plasmid pCZA141. For the purposes of all Figures, the IS493 arrow denotes the 5'→3' orientation of sequence as published and has no relationship to transcription or open reading frames.

The IS493 transposable element can be obtained from plasmid pZCA141, which can be conventionally isolated from *E. coli* K12 JM109/pCZA141, a strain deposited and made part of the permanent stock culture collection of the NRRL. A culture of *E. coli* K12 JM109/pCZA141 can be obtained from the NRRL under the accession number NRRL B18417. A restriction site and function map of plasmid pCZA141 is presented in FIG. 2 of the accompanying drawings. A variety of vectors can be constructed to utilize the integrating function of the IS493 transposable element, such as illustrative vectors pCZA152, pCZA153, pCZA154 and pCZA155.

Figure 3:
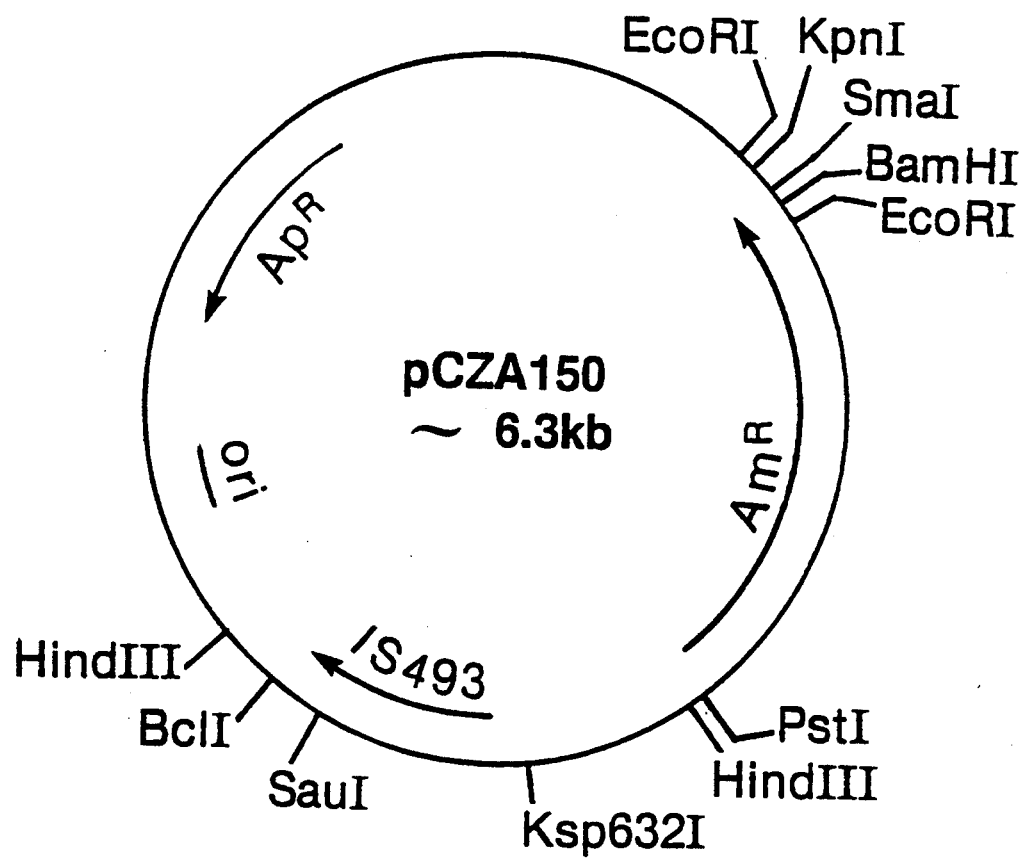
FIG. 3—the restriction site and function map of plasmid pCZA150.
Figure 3A:
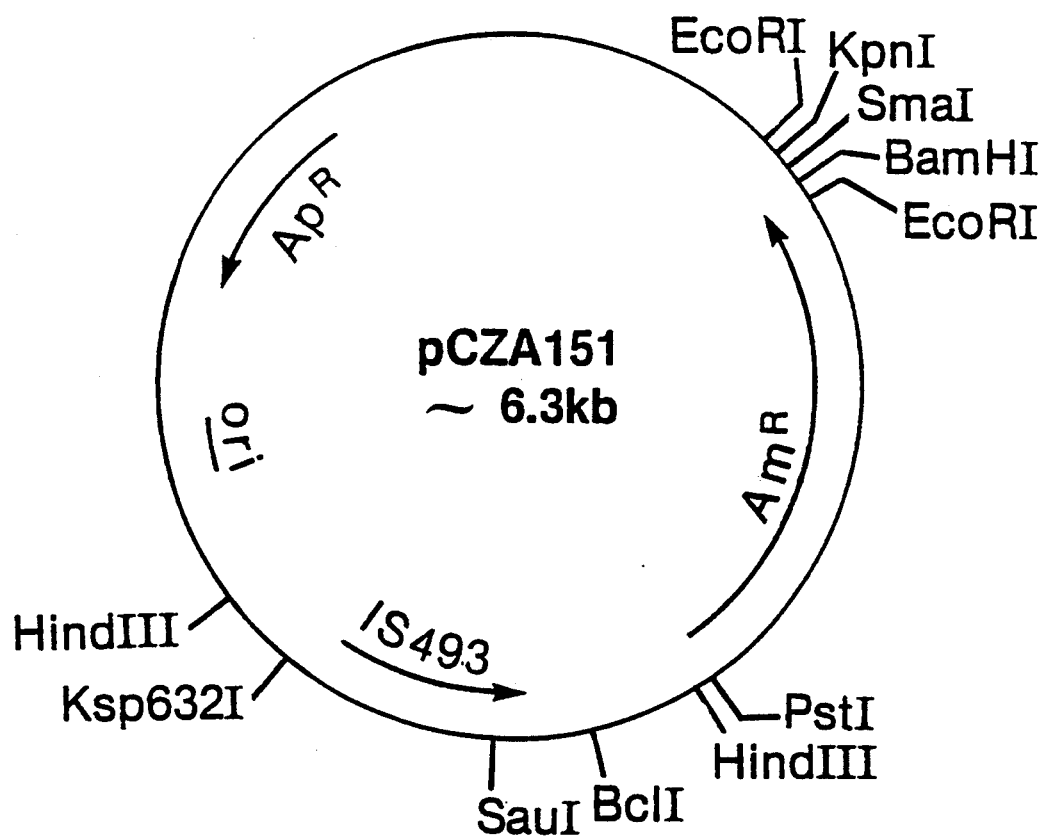
FIG. 3A—the restriction site and function map of plasmid pCZA151.

Plasmid pCZA150 is constructed by first isolating plasmid pKC462A from *E. coli* K12 SF8/pKC462A (NRRL B-15973). Plasmid pKC462A is digested with restriction enzymes PstI and BamHI and the ~1.5 kb restriction fragment is isolated. This restriction fragment contains the apramycin resistance-conferring gene. Plasmid pUC19 (BRL) is also digested with restriction enzymes PstI and BamHI, then the ~1.5 kb apramycin resistance-conferring restriction fragment is ligated into the PstI/BamHI cut plasmid pUC19 to form plasmid pOJ107. Next, plasmid pCZA141 is digested with restriction enzyme HindIII and the ~2.1 kb IS493-containing restriction fragment is isolated. This fragment is then ligated into HindIII digested plasmid pOJ107 to form plasmids pCZA150 and pCZA151, which differ only with respect to the orientation of the IS493-containing restriction fragment. The orientation of the IS493 element within these plasmids is determined by digesting the plasmids with restriction enzymes SauI and BamHI and checking for the presence of specific restriction fragments. These plasmids which contain ~2.9 kb and ~3.4 kb restriction fragments are designated plasmid pCZA150, while those plasmids which contain ~1.7 and 4.6 kb restriction fragments are designated plasmid pCZA151. Restriction site and function maps of plasmid pCZA150 and pCZA151 are presented in FIGS. 3 and 3A, respectively, of the accompanying drawings.

Figure 4:
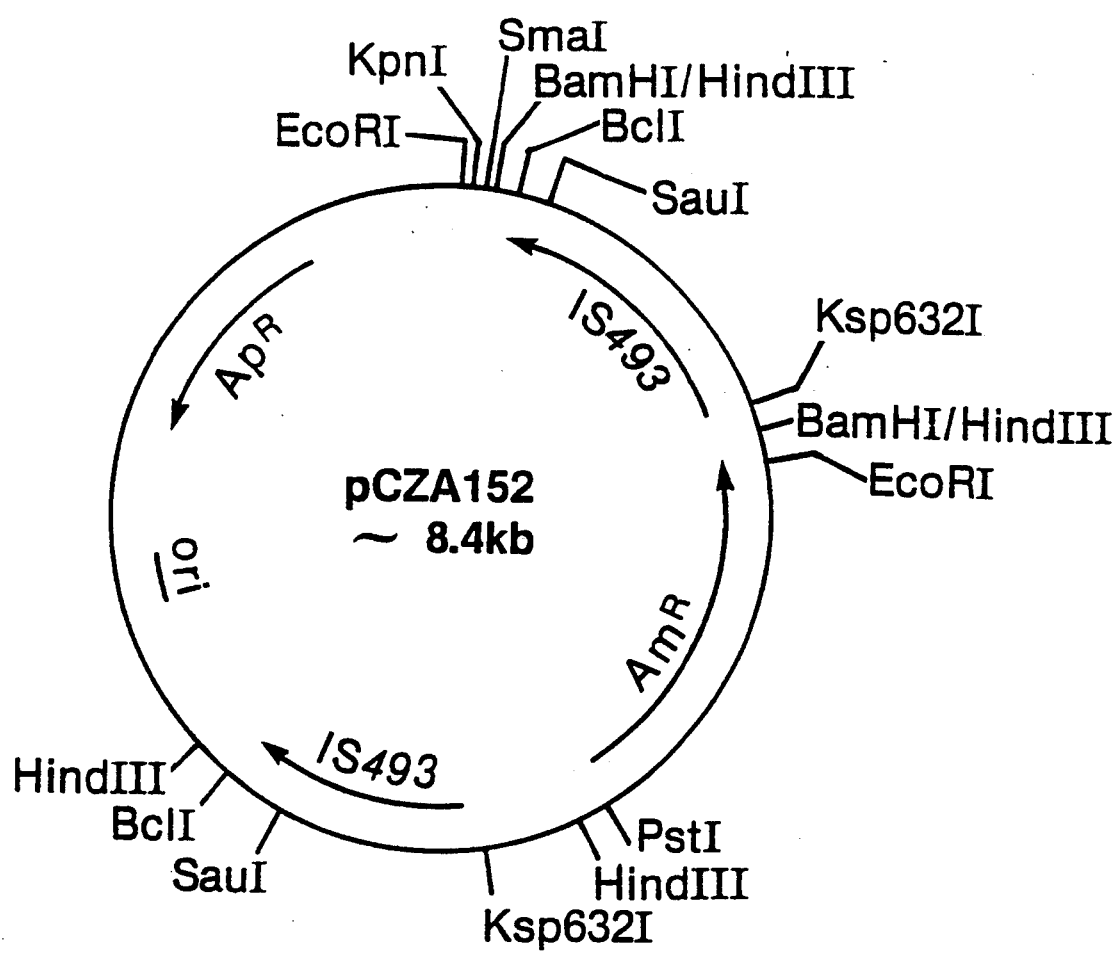
FIG. 4—the restriction site and function map of plasmid pCZA152.
Figure 4A:
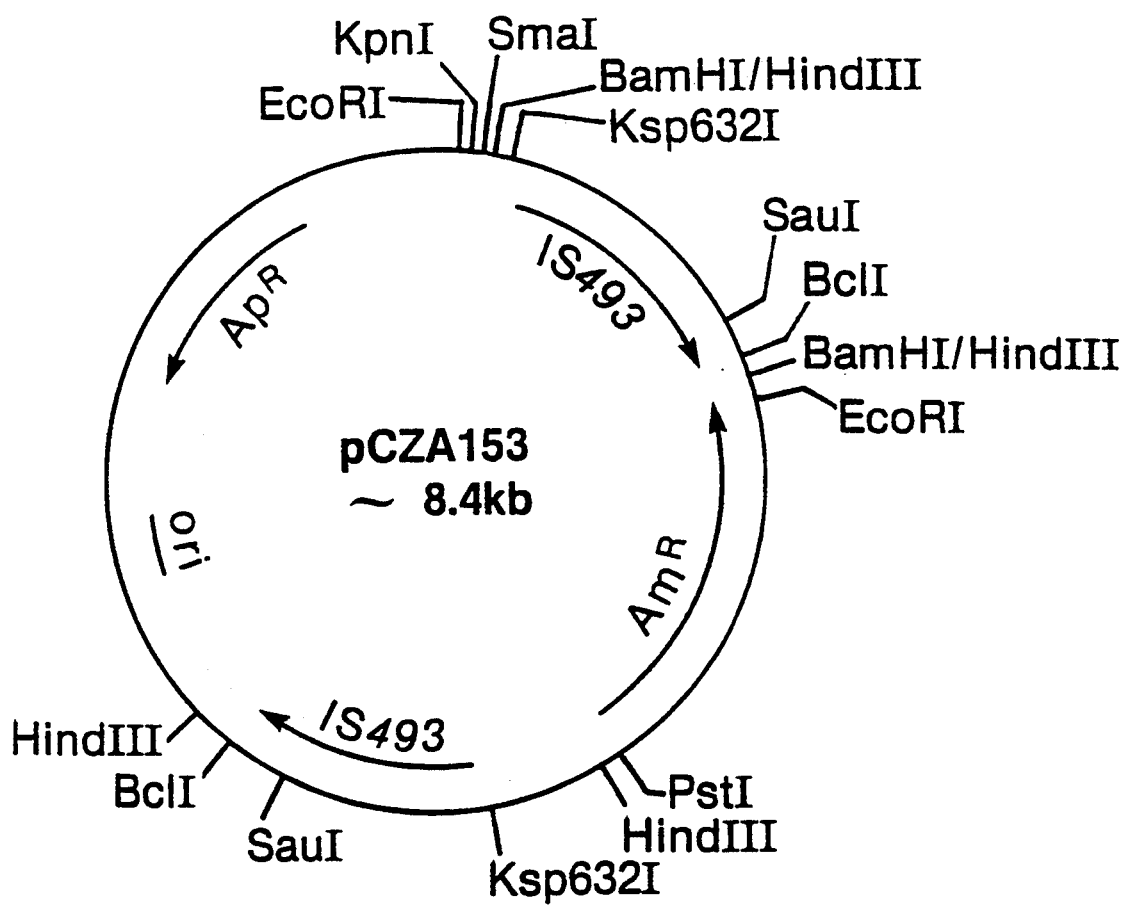
FIG. 4A—the restriction site and function map of plasmid pCZA153.

Plasmid pCZA150 is cut with restriction enzyme BamHI and, along with some of the ~2.1 kb, HindIII-cut, IS493 containing restriction fragment of plasmid pCZA141, is treated with mung bean nuclease to "blunt" the ends of the restriction sites. The "blunted" IS493 containing restriction fragment is then ligated into the BamHI digested, "blunted" pCZA150 to form plasmids pCZA152 and pCZA153, which differ only with respect to the orientation of the second IS493-containing restriction fragment. The orientation of this second IS493 element within these plasmids is determined by digesting the plasmids with restriction enzymes SauI and SmaI and checking for the presence of specific restriction fragments. The plasmids which contain ~2.93 kb, ~5.3 kb and ~0.23 kb restriction fragments are designated plasmid pCZA152, while those plasmids which contain ~3.63 kb, ~2.93 kb and 1.9 kb restriction fragments are designated plasmid pCZA153. Restriction site and function maps of plasmids pCZA152 and pCZA153 are presented in FIGS. 4 and 4A, respectively, of the accompanying drawings.

Figure 5:
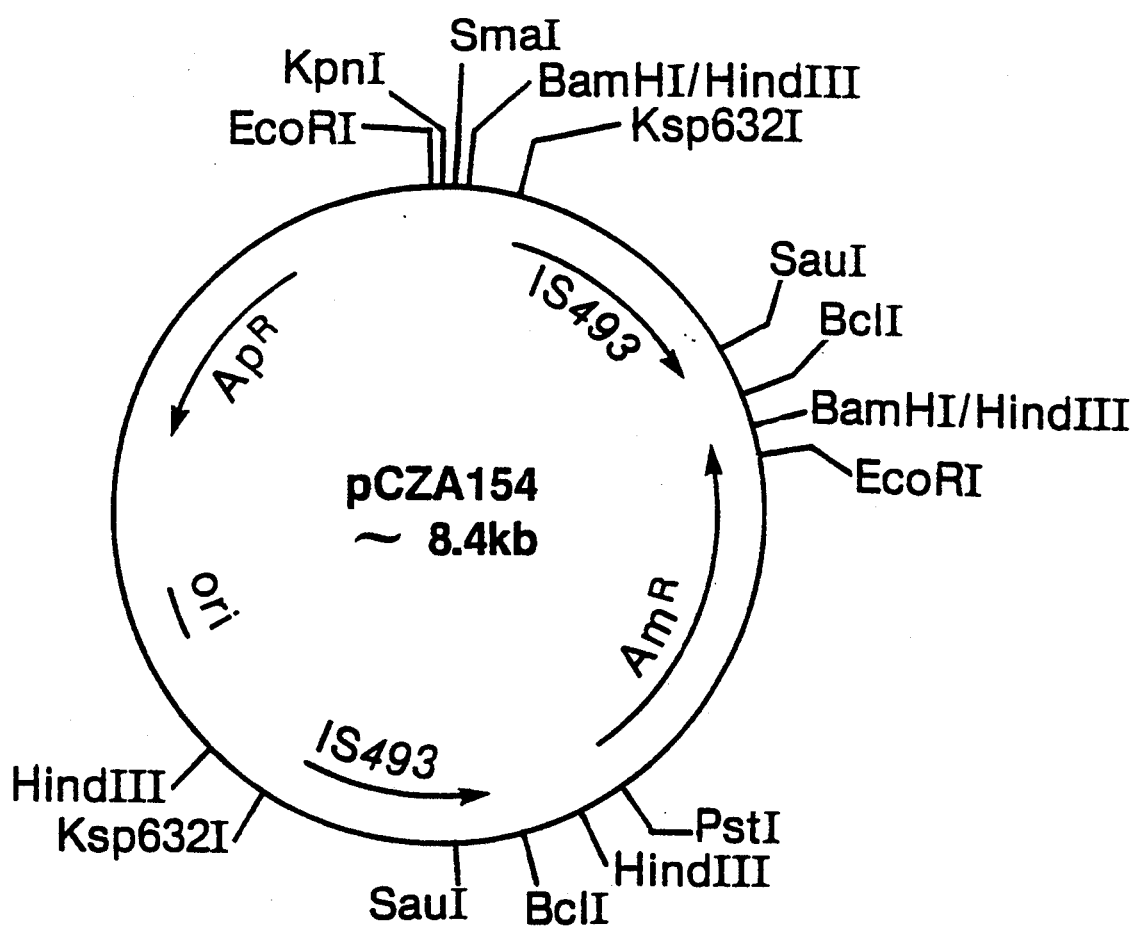
FIG. 5—the restriction site and function map of plasmid pCZA154.
Figure 5A:
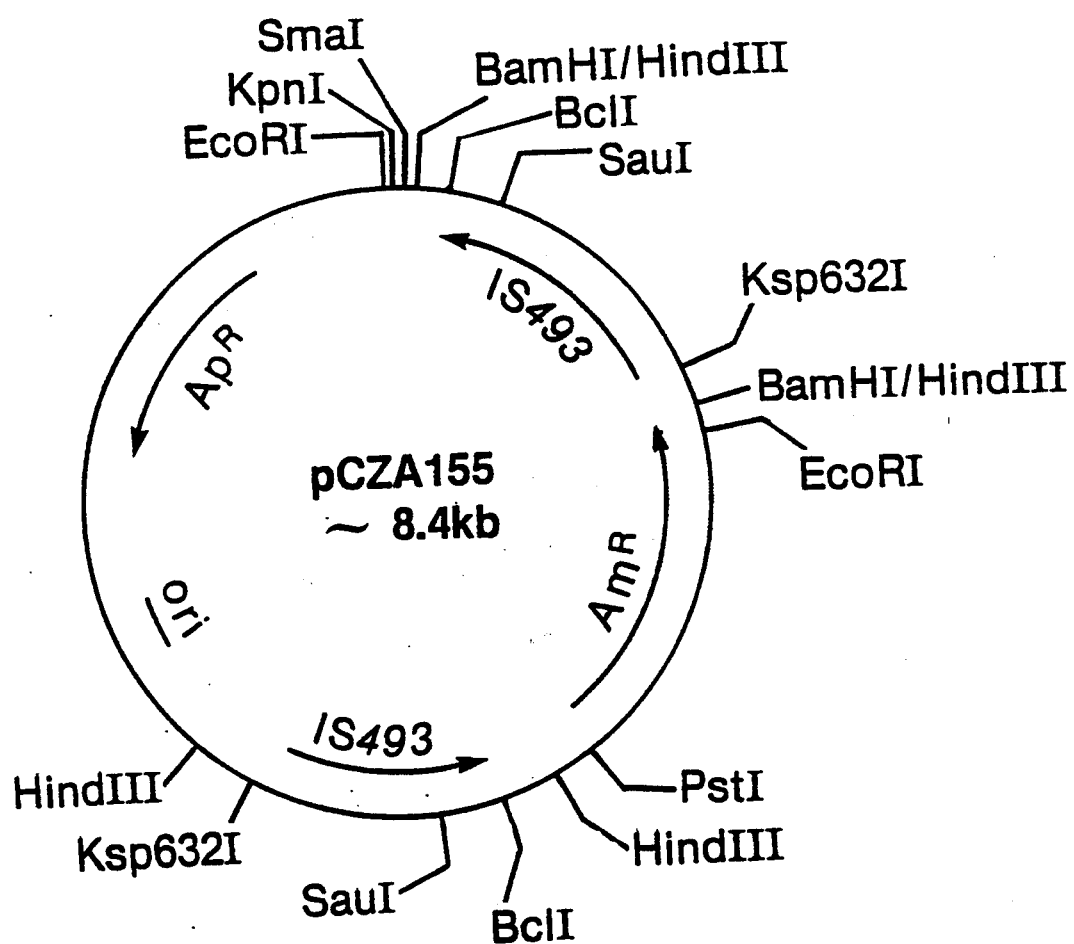
FIG. 5A—the restriction site and function map of plasmid pCZA155.

In the same manner, plasmid pCZA151 is cut with restriction enzyme BamHI and treated with mung bean nuclease. The "blunted" IS493 containing restriction fragment of pCZA141 is then ligated into the BamHI-digested, blunted pCZA151 to form plasmids pCZA154 and pCZA155, which differ only with respect to the orientation of the second IS493-containing restriction fragment. The orientation of the second IS493 element within these plasmids is determined by digesting the plasmids with restriction enzymes SauI and SmaI and checking for the presence of specific restriction fragments. The plasmids which contain ~1.96 kb, ~4.6 kb and ~1.9 kb restriction fragments are designated plasmid pCZA154, while those plasmids which contain ·3.63 kb, ~4.6 kb and ~0.23 kb restriction fragments are designated plasmid pCZA155. Restriction site and function maps of plasmids pCZA154 and pCZA155 are presented in FIGS. 5 and 5A, respectively, of the accompanying drawings. Transformation of a pool containing plasmids pCZA152, pCZA153, pCZA154 and pCZA155 into *Streptomyces lividans* CT2 results in transformed colonies which are resistant to the antibiotic apramycin. Inasmuch as none of the exemplified plasmids contain a Streptomyces-functional origin of replication, the appearance of apramycin resistant colonies will in many cases be due to transposition events wherein the apramycin resistance-conferring gene and flanking IS493 sequences have been incorporated into the *S. lividans* genome.

Transposition events, such as those made possible by IS493, are very useful because transposition may occur in a variety of locations in the genome and does not require DNA homology for integration. In addition, integration of DNA by transposition mechanisms is not limited to organisms that have functional homologous recombination systems. The IS493 transposable element is in no way limited to the use in the plasmids herein described, as many different techniques and cloning vectors could be used to introduce the transposable element into the host cell. Furthermore, the types of genes integrated into the chromosome via transposition using the IS493 element are also virtually limitless. The antibiotic resistance-conferring genes of the exemplified plasmids could be replaced by many different antibiotic resistance conferring genes or the antibiotic resistance-conferring genes could be replaced by heavy metal resistance-conferring genes or biosynthetic genes. The stable integration of biosynthetic genes into the chromosome of a host cell can cause increased production of the desired gene product or the production of new, hybrid gene products. Those skilled in the art recognize that virtually any gene encoding any function can be transposed into the host chromosome using the IS493 element disclosed herein. Therefore, the addition of any extraneous DNA within the parameters of the IS493 element would be within the scope of the present invention.

Many modifications and variations of the present illustrative DNA sequence are possible. Such modifications can introduce new restriction sites into the IS493 sequence and could greatly increase the utility of the element, provided the element retains the ability to transpose. Indeed, some modifications could potentially alter the frequency of transposition controlled by IS493 derivatives. These modified IS493 elements may occur naturally or can be produced by synthetic methods in substantial accordance with the procedures of Itakura et al., 1977, Science 198: 1056 and Crea et al., 1978, *Proc. Nat. Acad. Sci. USA* 75: 5765. In addition, synthetic components or linkers can be synthesized either by using a Systec 1450A DNA synthesizar (Systec Inc., 3816 Chandler Drive, Minneapolis, Minn.) or an ABS 380A DNA synthesizer (Applied Biosystems, Inc., 850 Lincoln Center Drive, Foster City, Calif. 94404). Many other DNA synthesizing instruments are known in the art and can be used to make synthetic DNA fragments. Therefore, the present invention is in no way limited to the DNA sequences and plasmids specifically exemplified.

The following examples further illustrate and also present a preferred embodiment of the invention disclosed herein. Both an explanation of and the actual procedures for constructing the invention are described where appropriate.

EXAMPLE 1

Isolation of Plasmid pCZA126

Plasmid pCZA126 can be obtained from the Northern Regional Research Center in *E. coli* K12 JM109 under the accession number NRRL B-18416. The lyophils of *E. coli* K12 JM109/pCZA126 are plated onto L-agar plates (10 g of Bacto-tryptone, 10 g of NaCl, 5 g of Bacto-Yeast Extract, and 15 g of agar per liter) containing 25 μg/ml ampicillin to obtain a single colony isolate of the strain. This colony is used to inoculate about 500 ml of L broth (L agar without agar) containing 25 μg/ml ampicillin, and the resulting culture is incubated at 37° C. with aeration until the cells reach stationary phase.

Plasmid DNA is obtained from the cells in accordance with the following procedure, which is adapted from Maniatis et al., 1982, *Molecular Cloning* (Cold Spring Harbor Laboratory). This same procedure is used, but on a smaller scale and with the ultracentrifugation steps replaced with phenol followed by chloroform extractions, to prepare the plasmid DNA used to identify the *E. coli* transformants.

About 500 ml of stationary-phase *E. coli*/pCZA126 cells are harvested by centrifugation at 4000×g for 10 minutes at 4° C., and the supernatant is discarded. The cell pellet is washed in 100 ml of ice-cold STE buffer (0.1M NaCl; 10 mM Tris-HCl, pH 7.8; and 1 mM EDTA). After the cell pellet is washed, the pellet is resuspended in 10 ml of Solution 1 (50 mM glucose; 25 mM Tris-HCl, pH=8.0; and 10 mM EDTA) that contains 5 mg/ml lysozyme and is left at room temperature for 10 minutes. Twenty ml of Solution 2 (0.2N NaOH and 1% SDS) are then added to the lysozyme-treated cells, and the solution is gently mixed by inversion. The mixture is incubated on ice for 10 minutes.

Fifteen ml of ice-cold, 3M sodium acetate, pH=4.8, are added to the lysed-cell mixture, and the solution is mixed by inversion. The solution is incubated on ice for 60 minutes. The 3M sodium acetate solution is prepared by mixing equal volumes of 3M acetic acid and 3M sodium acetate.

The lysed cell mixture is centrifuged in a Beckman SW27 rotor (or its equivalent) at 20,000 rpm for 20 minutes at 4° C. About 36 ml of supernatant are recovered, and 2.5 volumes of ethanol are added, mixed, and the resulting solution left on ice for 15 minutes. The plasmid DNA is collected by centrifugation at 12,000×g for 30 minutes at room temperature. The supernatant is discarded, and the DNA pellet is washed with 70% ethanol at room temperature. The ethanol wash is decanted, and the pellet is dried in a vacuum desiccator. The pellet is then resuspended in 8 ml of TE buffer.

Eight grams of CsCl are added to the DNA solution. About 0.8 ml of a 10 mg/ml solution of ethidium bromide in water are added for each 10 ml of CsCl-DNA solution. The final density of the solution is about 1.55 g/ml, and the ethidium bromide concentraton is about 800 μg/ml. The solution is transferred to a Beckman Type 50 centrifuge tube, filled to the top with TE buffer containing 1.55 g/ml CsCl, sealed, and centrifuged at 45,000 rpm for 24 hours at 20° C. After centrifugation, two bands of DNA are visible in ordinary light and become even more prominent in UV light. The cap is removed from the tube, and the lower DNA band is recovered using a syringe with a #21 hypodermic needle inserted through the side of the centrifuge tube.

The ethidium bromide is removed from the solution of plasmid DNA by several extractions with water-saturated 1-butanol, and the CsCl is removed by dialysis against TE buffer. After extractions with buffered phenol and then chloroform, the DNA is precipitated, washed with 70% ethanol, and dried. About 0.5 mg of plasmid pCZA126 DNA can be obtained by this procedure.

EXAMPLE 2

Construction of *Streptomyces lividans* CT2/pCZA126

A. List of Solutions

The following solutions are referred to throughout the Examples and are presented here for clarity.

| Ingredient | Amount |
| --- | --- |
| 1. P medium (~100 ml): | |
| Sucrose | 10.3 g |
| $K_2SO_4$ | 0.025 g |
| Trace element solution (see #3) | 0.2 ml |
| $MgCl_2.6H_2O$ | 0.203 g |
| Water | 80 ml |
| After autoclaving add: | |
| $KH_2PO_4$ (0.5%) | 1 ml |
| $CaCl_2.2H_2O$ (3.68%) | 10 ml |
| (N-tris-(hydroxymethyl)-methyl-2-aminoethane sulphonic acid), "TES" buffer, 0.25 M, pH = 7.2 | 10 ml |
| 2. Trace element solution (~1 L): | |
| $ZnCl_2$ | 40 mg |
| $FeCl_3.6H_2O$ | 200 mg |

-continued

| Ingredient | Amount |
| --- | --- |
| $CuCl_2.2H_2O$ | 10 mg |
| $MnCl_2.4H_2O$ | 10 mg |
| $Na_2B_4O_7.10H_2O$ | 10 mg |
| $(NH_4)_6Mo_7O_{24}.4H_2O$ | 10 mg |
| $H_2O$ | 1 L |

3. Modified R2 Regeneration Medium (~1 L):

| | |
| --- | --- |
| Sucrose | 103 g |
| $K_2SO_4$ | 0.25 g |
| Trace element solution | 2 ml |
| $MgCl_2.6H_2O$ | 10.12 g |
| glucose | 10 g |
| L-asparagine.$1H_2O$ | 2.0 g |
| casamino acids | 0.1 g |
| Agar | 22 g |
| Water | to 700 ml |

The pH is adjusted to pH=7.2 before autoclaving. After autoclaving, add:

| | |
| --- | --- |
| $KH_2PO_4$ (0.05 g/100 ml) | 100 ml |
| $CaCl_2$ (2.22 g/100 ml) | 100 ml |
| TES Buffer (5.73 g/100 ml, pH = 7.2) | 100 ml |

4. YMX Agar is 0.3% yeast extract, 0.3% malt extract, 0 2% dextrose and 2.0% agar.
5. TSB—Trypticase Soy Broth is made at 30 g/l and is obtained from Baltimore Biological Laboratories (BBL), P.O. Box 243, Cockeysville, Md. 21031.

B. Transformation of *Streptomyces lividans* CT2

*Streptomyces lividans* CT2 (NRRL 18418) is plated on YMX agar and incubated at 30° C. for about 72 hours. A plug of cells is removed from the plate and used to inoculate 10 ml of TSB. The culture is homogenized and incubated at 30° C. for ~30 hours. About 4 ml of this culture are homogenized and used to inoculate 100 ml of TSB containing 0.4% glycine. The culture is incubated at 30° C. for about 24 hours. About 4 ml of this culture are again homogenized and used to inoculate 100 ml of TSB containing 0.4% glycine. The culture is incubated at 30° C. for about 16 hours. The cells are harvested and washed three times with 10.3% sucrose. The cells are resuspended in 100 ml of P media containing 1 mg/ml lysozyme, and the resulting solution is incubated at 30° C. for 2 hours. During this protoplasting step, the cells are pipetted up and down to disperse clumps. The protoplasts are collected and washed three times with P medium. The protoplasts are then suspended in 10 ml of P medium. This process usually generates about 2 to $5 \times 10^7$ protoplasts per 150 µl of solution.

Approximately 150 µl of the protoplast solution are added to 10 µl of the transforming DNA, either in ligation or TE buffer, and mixed. About 100 µl of 50% polyethylene glycol 1000 in P media are then added and mixed. After a brief (1 to 2 minutes) incubation at room temperature, the cell-DNA mixture is brought to a volume of 1 ml by the addition of P media. The cell suspension is plated onto modified R2 generation medium; about 0.1 ml of cells is inoculated per R2 plate. The plates are incubated at 30° C. overnight (~16 hours) and then overlaid with ~3 ml of R2 agar overlays (103 g sucrose, 10.12 g $MgCl_2$, 2.22 g $CaCl_2$, 4.1 g agar, and 5.72 g TES at pH=7.2 per liter) containing enough thiostrepton to give a final concentration, after diffusion, of 25 µg/ml. The plates are then incubated for about four days at 30° C., when colonies become visible to the naked eye.

The single colonies were then used to inoculate 10 ml TSB cultures containing 25 µg/ml thiostrepton. The cultures were homogenized and then grown overnight at 30° C. in a rotary shaker.

Plasmid isolation for analysis and confirmation of structurally intact plasmid pCZA126 is done as follows.

The mycelium is collected by centrifugation, washed twice with 10.3% sucrose and then suspended in 1-2 ml of 10.3% sucrose. Four hundred µl of the cell mixture are transferred to a small tube, and 100 µl of 5× Lysozyme solution (125 mM Tris-HCl, pH8; 125 mM EDTA, pH8; 10.3% sucrose; 10 mg/ml Lysozyme) are added. The suspension is incubated at 30° C. for 30-60 minutes, followed by the addition and mixing of 300 µl of 0.3M NaOH containing 1% SDS. The latter solution is kept at 50° C. before its addition to the cell mix. The cell mixture is placed at 80° C. for 10 minutes, cooled to room temperature, and then extracted with 200 µl of phenol:$CHCl_3$ (50:50). The aqueous phase is transferred to a clean tube, made 0.3M in NaOAc, and then, one volume of isopropanol is added. The DNA is incubated at room temperature for five minutes and then pelleted by centrifugation. The pellet is dissolved in 500 µl of TE buffer, and about 25 µl of 0.1M spermine are added to the solution of DNA, and the mixture is incubated at room temperature for 5 minutes. After centrifugation, the DNA pellet is rinsed with 75% ethanol, then resuspended and reprecipitated from 0.3M sodium acetate using ethanol. After this last precipitation, the plasmid DNA is suspended in 50 µl of TE buffer. Restriction enzyme cutting and electrophoretic analysis of the reaction products are used to confirm plasmid structure.

EXAMPLE 3

Isolation of Plasmid pCZA126 from *Streptomyces lividans*

The culture isolated in Example 2 is grown to stationary phase in TSB plus 25 µg/ml thiostrepton and homogenized. Five ml of the homogenized culture are used to inoculate 100 ml of TSB also containing 25 µg/ml thiostrepton. The 100 ml of culture are incubated at 30° C. with aeration until the *Streptomyces lividans*/pCZA126 cells reach stationary phase.

The cells are collected and washed once with a 10.3% sucrose solution. The cells are then suspended in 24 ml of 10.3% sucrose, and 6 ml of 5×lysozyme solution are added. The solution is mixed and then incubated at 30° C. for 30-60 minutes, and then, about 18 ml of a solution that is 0.3M NaOH, 1% SDS, and prewarmed to 50° C. are added, mixed and the resulting mixture is incubated at 80° C. for 10 minutes. The mixture is then cooled to room temperature, and 12 ml of a solution made by mixing 500 g phenol and 500 g $CHCl_3$ in 200 ml $H_2O$ are added and mixed well with the cell-extract. The phases are separated by centrifugation at 6000-8000 rpm for 10 minutes; approximately 45 ml of the resulting upper phase are transferred to a clean bottle.

Next, 4.5 ml of 3M sodium acetate (NaOAc) and 50 ml of isopropanol are added to the supernatant, and the solution is mixed and left at room temperature for 30 minutes. The solution is then centrifuged (8000 rpm for 30 minutes) and the resulting supernatant discarded. The pellet is resuspended in 10 ml of TE buffer (10 mM Tris-HCl, pH=8, and 1 mM EDTA) containing 9.5 g of CsCl. About 1 ml of a 5 mg/ml solution of ethidium bromide is added to the solution to bring the final volume to 12.5 ml. The solution is then centrifuged at 52,000 rpm for 48 hours at 20° C. in a Beckman Ti-75 fixed-angle rotor. The fraction containing the plasmid band is extracted 5 times with isopropanol saturated with 20× SSC (0.3M NaCl and 0.3M NaCitrate) to remove the ethidium bromide. After the extractions, the sample is dialyzed against 1000 volumes of H$_2$O and then against 1500 volumes of TE buffer. The procedure yields about 50 μg of plasmid pCZA126 DNA at a concentration of ~0.2 μg/μl and is stored at 4° C.

EXAMPLE 4

Transformation of E. coli JM109 and Selection of Plasmids Containing a Transposable Element The plasmids isolated from *Streptomyces lividans* CT2 are then back-transformed into competent *Escherichia coli* K12 JM109 obtained from Stratagen (11099 North Torrey Pines Rd., LaJolla, Calif. 92037). A 0.1 ml aliquot of the cells was added to about 0.1 μg of the DNA from the previous Example. The cell-DNA mixture was incubated on ice for one hour, heat-shocked at 42° C. for 90 seconds, and then chilled on ice for two minutes. The DNA and cell mixture was added to a tube containing 0.9 ml L medium with 10 mM MgSO$_4$, 10 mM MgCl$_2$ and 10 mM glucose, then the mixture was incubated for 45 minutes at 30° C. with gentle shaking.

Aliquots of the transformation mixture are plated on L-agar plates containing 25 μg/ml ampicillin and 25 μg/ml apramycin. Alternatively, 25 μg/ml carbencillin (Sigma) may be used in place of ampicillin. The plates were then incubated at 30° C. for 48 hours. Many colonies which grow in the presence of both ampicillin and apramycin will arise from clones which have a non-functional cI857 repressor gene in their plasmids. Approximately one tenth of the transformation mixture is also plated on L-agar containing only ampicillin at 25 μg/ml, to check the transformation frequency against the frequency of disruption of the repressor gene. Plasmid DNA is isolated, in substantial accordance to the teaching of Example 1, from colonies resistant to both ampicillin and apramycin.

The repressor gene of plasmid pCZA126 is located on a PstI restriction fragment. The plasmid DNA from each isolate purified above was digested with PstI to check for possible insertions of transposable elements. Approximately 0.5 μg plasmid DNA in 10 μl H$_2$O is mixed with 2 μl of 10× PstI buffer (100 mM Tris-HCl, pH 7.5, 1M NaCl, and 100 mM MgCl$_2$), 7 μl H$_2$O and 1 μl (~15 units; unit definitions herein correspond to those of New England Biolabs, 32 Tozer Road, Beverly, Mass. 01915-9990, unless otherwise indicated) of restriction enzyme PstI. The resulting reaction is incubated at 37° C. for two hours.

The DNA is electrophoresed on a 1% agarose gel and the DNA bands are visualized by long-range UV light after staining with ethidium bromide. A small number of the plasmids contain an ~1.2K PstI restriction fragment which corresponds to the expected size of the natural cI857 gene-containing DNA fragment. The clones carrying these plasmids probably became apramycin resistant due to a simple point mutation in the cI857 gene or spontaneous chromosomal apramycin resistance. The number of these colonies with spontaneous chromosomal apramycin resistance can be reduced by plating the cells on a media containing ampicillin or carbenicillin since this selects for a subpopulation consisting of only those cells that have been transformed with plasmid. Some plasmids, however, demonstate a large, ~2.8 kb PstI fragment, which corresponds to the ~1.2 kb repressor gene fragment with an inserted transposable element of ~1.6 kb. This transposable element is designated IS493. Further selective plating would result in recovery of other transposable elements. Transposition is a relatively rare event, therefore plasmid pCZA126 is a very powerful tool for the selection of insertion sequences and transposons.

EXAMPLE 5

Construction of Plasmids pCZA150, pCZA151, pCZA152, pCZA153, pCZA154 and pCZA155

A. Construction of Plasmid pOJ107

Plasmid pKC462A is obtained from the Northern Regional Research Center in *E. coli* K12 SF8/pKC426A under the accession number NRRL B-15973. A restriction site and function map of plasmid pKC462A is presented in FIG. 3 of the accompanying drawings. Plasmid DNA is extracted from the cells in substantial accordance with the teaching of Example 1. The apramycin resistance-conferring gene of plasmid pKC462A is found on an approximately 1.5 kb BamHI-PstI restriction fragment. To isolate this fragment, about 1 μg of plasmid pKC462A DNA in 10 μl H$_2$O is mixed with 2 μl 10× PstI buffer, 7 μl H$_2$O and 1 μl restriction enzyme PstI. After incubation at 37° C. for one hour, 3 μl of 10× BamHI buffer (200 mM Tris.HCl (pH 8.0), 1M NaCl and 70 mM MgCl$_2$), 6 μl of H$_2$O and 1 μl restriction enzyme BamHI is added to the mixture and incubation is allowed to continue for another hour at 37° C.

The PstI-BamHI digested plasmid pKC462A is then electrophoresed on a 1% agarose gel until the desired ~1.5 kb restriction fragment is clearly separated from the other digestion products. Visualization of the electrophoresed DNA is accomplished by staining the gel in a dilute solution (0.5 μg/ml) of ethidium bromide and exposing the stained gel to long-wave UV light. After the desired fragment is located, a small slit is made in the gel in front of the fragment, and a small piece of Schleicher and Schuell (Keene, NH 03431) NA-45 DEAE membrane was placed in the slit. Upon further electrophoresis, the ~1.5 kb PstI-BamHI restriction fragment is non-covalently bound to the DEAE membrane. After the desired fragment is bound to the DEAE membrane, the membrane is removed and rinsed with low salt buffer (150 mM NaCl; 0.1 mM EDTA; and 20 mM Tris-HCl, pH=8). Next, the membrane is placed in a small tube and immersed in high salt buffer (1M NaCl; 0.1 mM EDTA; and 20 mM Tris-HCl, pH=8) and then incubated at 65° C. for one hour to elute the DNA from the DEAE paper. After the 65° C. incubation, the incubation buffer is collected and the membrane rinsed with high salt buffer. The rinse solution is pooled with the incubation buffer before collecting the desired DNA fragments.

In the same manner, plasmid pUC19 (available from BRL, Gaithersburg, Md. 20877) is also digested with restriction enzymes PstI and BamHI, then electrophoresed and the ~2.7 kb vector fragment is isolated as above. The purified, digested vector fragment of pUC19 is then resuspended in 50 μl TE buffer. The PstI-BamHI-digested plasmid pUC19 DNA (1 μl) is added to 10 μl (~0.5 μg) of the ~1.5 kb, apramycin resistance-conferring BamHI-PstI restriction fragment of plasmid pKC462A, 2 μl of 10× ligase buffer (660 mM Tris.HCl, pH=8; 66 mM MgCl$_2$; 10 mM dithiothreitol (DTT); and 10 mM ATP), and 6 μl of H$_2$O. About 1 μl (~100 units) of T4 DNA ligase is added to the solution of DNA, and the resulting reaction is incubated at 15° C. overnight (~16 hours). The ligation results in an ~4.2 kb plasmid designated as plasmid pOJ107. A restriction site and function map of plasmid pOJ107 is presented in FIG. 3 of the accompanying drawings.

To prepare *E. coli* K12 MM294 cells that are competent for transformation, the lyophils of *E. coli* K12 MM294 obtained from the NRRL (accession number NRRL B-15625) are reconstituted to isolate single colonies. One single-colony isolate of MM294 is inoculated into 5 ml of L broth and the culture is incubated at 37° C. overnight with aeration. Fifty μl of the overnight culture are used to inoculate 5 ml of L broth. The culture is incubated at 37° C. overnight with aeration. The following morning, the culture is diluted to 200 ml with L broth. The diluted culture is incubated at 37° C. with aeration until the absorbance at 550 nm ($A_{550}$) is about 0.5, which indicates a cell density of about $1 \times 10^8$ cells/ml. The culture is cooled for ten minutes in an ice-water bath, and the cells are then collected by centrifugation at 4000×g for 10 minutes at 4° C. The cell pellet is resuspended in 100 ml of cold 10 mM NaCl and then immediately repelleted by centrifugation. The cell pellet is resuspended in 100 ml of 30 mM CaCl$_2$ and incubated on ice for 20 minutes.

The cells are again collected by centrifugation and resuspended in 10 ml of 30 mM CaCl$_2$. A one-half ml aliquot of the cells was added to the ligated DNA prepared above. The cell-DNA mixture is incubated on ice for one hour, heat-shocked at 42° C. for 90 seconds, and then chilled on ice for about two minutes. The cell-DNA mixture is centrifuged, and the cell pellet is resuspended into 0.5 ml of L broth in a 1.5 ml tube and incubated at 37° C. for one hour.

Aliquots of the transformation mixture are plated on L-agar plates containing 100 μg apramycin/ml. The plates are incubated at 37° C. overnight. Several apramycin-resistant colonies are selected and then screened by restriction enzyme analysis of their plasmid DNA for the presence of the ~1.5 kb PstI-BamHI restriction fragment. Plasmid DNA is obtained from the *E. coli* K12 MM294 pOJ107 transformants in substantial accordance with the teaching of Example 1.

B. Construction of Plasmids pCZA150 and pCZA151

Plasmid pCZA141, which contains IS493 on an approximately 2.1 kb HindIII restriction fragment is obtained from the NRRL from *E. coli* K12 JM109/pCZA141 under the accession number NRRL B-18417. A restriction site and function map of plasmid pCZA141 is presented in FIG. 2 of the accompanying drawings. Plasmid DNA is extracted from the cells in substantial accordance with the teaching of Example 1, then about 5 μg of plasmid pCZA141 are digested in substantial accordance with the teaching of Example 5A, except 1 μl HindIII restriction enzyme and 2 μl 10× HindIII buffer (500 mM Tris.HCl (pH=8.0), 100 mM MgCl$_2$ and 500 mM NaCl) are used. Following this HindIII digestion, the ~2.1 kb HindIII restriction fragments are isolated from an agarose gel in substantial accordance with the teaching of Example 5A.

About 1 μg of plasmid pOJ107 is then digested with restriction enzyme HindIII and the linear vector is isolated as taught above. The ~2.1 kb HindIII restriction fragment of plasmid pCZA141 is then ligated into the HindIII-digested vector pOJ170 in substantial accordance with the teaching of Example 5A. Following transformation of the ligation mixture into *E. coli* MM294 cells, the plasmids isolated from the resultant apramycin resistant colonies are analyzed by restriction digestion. Those plasmids which contain ~2.9 kb and ~3.4 kb SauI-BamHI restriction fragments are designated plasmid pCZA150, while those plasmids which contain ~1.7 kb and ~4.6 kb SauI-BamHI restriction fragments are designated plasmid pCZA151. Restriction site and function maps of plasmids pCZA150 and pCZA151 are presented in FIGS. 3 and 3A, respectively, of the accompanying drawings.

C. Construction of Plasmids pCZA152, pCZA153, pCZA154 and pCZA155

About 10 μg of plasmid pCZA150 is digested with restriction enzyme BamHI in substantial accordance with the teaching of Example 5A. This linear vector fragment is then purified and dissolved in 90 μl of H$_2$O and 10 μl of 10× Mung Bean Nuclease buffer (300 mM NaAcetate, pH=4.6; 500 mM NaCl and 10 mM ZnCl$_2$). Ten units of Mung Bean Nuclease (Pharmacia) is added and the mixture is incubated for 10 minutes at 37° C., then extracted with a 1:1 mixture of phenol/chloroform. A 1:10 volume of 3M NaAcetate is added to the aqueous phase along with 3 volume of ethanol. Following a ten minute incubation at −70° C., the sample is centrifuged for 5 minutes in an Eppendorf centrifuge and the liquid is discarded. The pellet is rinsed with 70% ethanol, then air dried and resuspended in 20 μl TE.

In the same manner, about 1 μg of the ~2.1 kb HindIII restriction fragment of plasmid pCZA141 (isolated in Example 5B) is also treated with Mung Bean Nuclease to create blunt ends. These blunt ended ~2.1 kb HindIII restriction fragments of plasmid pCZA141 are then ligated into the BamHI-cut, Mung Bean Nuclease treated plasmid pCZA150 in substantial accordance with the teaching of Example 5A. After transformation into *E. coli* K12 MM294 cells, the plasmids isolated from apramycin resistant colonies are digested with restriction enzymes SauI and SmaI. Those plasmids which contain ~5.3 kb, ~2.93 kb and ~0.23 kb restriction fragments are designated plasmid pCZA152, while those plasmids which contain ~3.63 kb, ~2.93 kb and ~1.9 kb restriction fragments are designated plasmid pCZA153. Restriction site and function maps of plasmids pCZA152 and pCZA153 are presented in FIGS. 4 and 4A, respectively, of the accompanying drawings.

About 10 μg of plasmid pCZA151 is digested with restriction enzyme BamHI and treated with Mung Bean Nuclease as taught above. About 1 μg of the ~2.1 kb HindIII-cut, Mung Bean Nuclease treated restriction fragment from plasmid pCZA141 is then ligated into the BamHI-cut, Mung Bean Nuclease treated plasmid pCZA151 in substantial accordance with the teachings above. After transformation into *E. coli* MM294 cells, the plasmids isolated from apramycin resistant colonies are digested with restriction enzymes SauI and SmaI. Those plasmids which contain ~4.6 kb, ~1.96 kb and ~1.9 kb restriction fragments are designated plasmid pCZA154, while those plasmids which contain ~4.6 kb, ~3.63 kb and ~0.23 kb restriction fragments are designated plasmids pCZA155. Restriction site and function maps of plasmids pCZA154 and pCZA155 are presented in FIGS. 5 and 5A, respectively, of the accompanying drawings.

A pool of plasmids pCZA152, pCZA153, pCZA154 and pCZA155 is next transformed into *Streptomyces lividans* CT2 in substantial accordance with the teaching of Example 2. The plated cells are covered with an apramycin overlay at a final concentration of 25 μg/ml. The emergence of apramycin resistant colonies demonstrates a transposable event wherein the apramycin resistance-conferring gene has been integrated into the *Streptomyces lividans* chromosome.

I claim:

1. A recombinant DNA compound comprising the transposable element IS493, wherein one strand of the DNA sequence comprises:

| | | |
|---|---|---|
| 5'-AGCGTTTTCC | ATCCTCAAGC | TGAGCTGGCC |
| TGATGCAGGC | AGAGGACGGC | CTGGACGAGG |
| ACCGTGACGC | GGGTGGTCGA | GCAACGGAGC |
| CTGCGAAGGA | GTCGCCAGGA | CTTGAGGGTC |
| GCGACGGCTT | GCTCGACGAG | CGCCCGGATC |
| TTCGCGTGGG | ATCGATTGAC | GGCCTGCTGC |
| CCTGCAGAGA | GCGTCTCCCA | CCGGCCGCGG |
| TAGGGAACAC | GGACCGTGCC | TCCGGCGCCC |
| TGGTAGCCCT | TGTCTGCCCA | GCAGTTGACG |
| TCGGCTGTGG | CAAGCGTGTC | GATGATGCCG |
| TGCTCGCGGG | CCGCACGGAC | GTCGTGGACG |
| GCTCCGGGCA | GGGCCGGCGA | GGCCCACAGC |
| AGGCGGCCGG | AAGGATCTGC | GATCACCTGT |
| ACGTTCATCC | CGTGTTTCTT | GTGCTTGCCC |
| GAGTAGAAAG | GCCGGTCGGC | GGCGATTCGG |
| TCGATCGGCA | GCAGCGTCCC | GTCCAGCAGG |
| ACGAACGCCT | TCATCGACGC | CGCCCGGACC |
| GCCTCGGCGA | GCGTCGGGGC | AAGGGCGGCC |
| AGAACCTCAG | CTGCCTCGGT | GACGTAGCGG |
| TAGGCAGTGG | TGGTGCCCAC | GCCGAACCCG |
| GCCGCGAGCT | GCACATACGG | ATGACCGTTG |
| CGGAGATGGG | CGAGGGCGAG | CAGAGCCTGC |
| CGACCTGCGC | TCAGGCGCCG | CCACCGGGTG |
| CCGAGACCAC | GGCGGTGTTC | CCGCAGACGG |
| GCGGAGAGGA | AGCGGAGGGC | AGAACTGGAC |
| ACGTCCAGCC | CGGAGGGGTA | AACAAGCACG |
| TGAAGCCTCT | AGTAGAGACG | GATTTCTTGG |
| TCGAAAACCC | ATCTACCAGG | GGCTTCACCC |
| CTGTGTCAGG | CCAACCCGCA | AGCTGCCGAA |
| GCAGAATGAA | GACGCTCCTT | GGCTACCGGT |
| CTGGCGCATG | CGAACCCCGA | CGTCGTGGGT |
| CTAGCTGGTT | GTCCTGACGG | GTGCGCTGCT |
| GCGCCCGTGG | CGTCGACCGC | TGAGCTCGGC |
| GTCGAGTGTC | TCCTGAGCCA | CGCGCATGGC |
| CTCGGCGTAT | ACGGGGTCCT | GCAGCCGCTT |
| CCACATCTCG | CCCTCAGAGA | CGICCTCAAC |
| GCAGCTGACC | ACCCACCAGA | TATTGCCGAA |
| GGGGTCCTTG | ATGCGCCCTC | CGCGCTGTCC |
| GAAGGCGTCG | TCGGCCAGGG | AAGTGACGAC |
| ATAGCCGCCA | GCTGCGACGG | CCTGGGAAAA |
| CGCCTCGTCC | GCATCGGCGA | CAAATACGCG |
| CAGCAGGCTC | GGCATGGCGG | GCCAGTCCGT |
| GTGTCGGTCG | AAGGCCAACA | CGACGGTGTC |
| GCCGACTCGG | ATCTCAGCGT | GACCGATCAA |
| GCCCTCCTCG | GTCGACACCC | GCCCGAGTTC |
| CTCGCCCCCG | AATGCCTGGG | TGACGAAGTC |
| GAGGAAAGCC | CCCGTGTCGT | CGGTGACGAC |
| CCAGGGCGCA | ACGGTGGTGT | AGCCCTCCGG |
| CTCGGGGCTG | GTCTGCTGGG | GCATCGCGGT |
| CCTTTCGCTG | ATGTTGCTTG | CCAGCAGCGA |
| CGGTAGGCGT | GAGCTAGGGT | CAGCTTCTGT |
| CCTAGACGGC | AGTGAGCTTC | GAGCGCAACC |
| GGTACTACCT | CACGACCGCT | CGCGCTGATC |
| CAGACCCCGC | CTCTGACCCC | TGACCCCGTC |
| AGCCTGAGGT | TGAAAAACGC | T-3' | wherein
A is deoxyadenyl
C is deoxycytidyl
G is deoxyguanyl, and
T is thymidyl.

2. A recombinant DNA cloning vector which comprises the IS493 sequence of claim 1.

3. The recombinant DNA cloning vector of claim 2 which is a phage.

4. The recombinant DNA cloning vector of claim 2 which is a plasmid.

5. The recombinant DNA cloning vector of claim 4 that is plasmid pCZA141.

6. The recombinant DNA cloning vector of claim 4 that is plasmid pCZA150.

7. The recombinant DNA cloning vector of claim 4 that is plasmid pCZA151.

8. The recombinant DNA cloning vector of claim 4 that is plasmid pCZA152.

9. The recombinant DNA cloning vector of claim 4 that is plasmid pCZA153.

10. The recombinant DNA cloning vector of claim 4 that is plasmid pCZA154.

11. The recombinant DNA cloning vector of claim 4 that is plasmid pCZA155.

* * * * *

UNITED STATES PATENT AND TRADEMARK OFFICE
CERTIFICATE OF CORRECTION

PATENT NO. : 5,382,527
DATED : January 17, 1995
INVENTOR(S) : Patricia J. Solenberg It is certified that error appears in the above-indentified patent and that said Letters Patent is hereby corrected as shown below:

Column 18, Line 2, delete "CGICCTCAAC", and insert therefor --CGTCCTCAAC--

Signed and Sealed this

Twenty-second Day of October, 1996

Attest:

BRUCE LEHMAN

Attesting Officer       Commissioner of Patents and Trademarks